United States Patent [19]

Iqbal et al.

[11] 4,385,174
[45] May 24, 1983

[54] ISOINDOLINE COMPOUNDS AND THE MANUFACTURE AND USE THEREOF

[75] Inventors: Abul Iqbal, Ettingen; Paul Lienhard, Frenkendorf, both of Switzerland

[73] Assignee: Ciba-Geigy Corporation, Ardsley, N.Y.

[21] Appl. No.: 242,005

[22] Filed: Mar. 9, 1981

[30] Foreign Application Priority Data

Mar. 13, 1980 [CH] Switzerland ............ 1976/80

[51] Int. Cl.$^3$ ............ C07D 403/12; C07D 413/12; C07D 417/12
[52] U.S. Cl. ............ 542/417; 544/225; 546/6; 546/7; 548/105; 548/106; 548/471; 548/403; 260/165
[58] Field of Search ............ 542/417; 544/225; 546/6, 7; 548/105, 106; 260/326.1

[56] References Cited

U.S. PATENT DOCUMENTS

4,022,770  5/1977  L'Eplattier ............ 548/105

*Primary Examiner*—Arthur P. Demers
*Attorney, Agent, or Firm*—Luther A. R. Hall

[57] ABSTRACT

The invention relates to a simplified process for the manufacture of 1:1 metal complexes of isoindoline azines of the formula

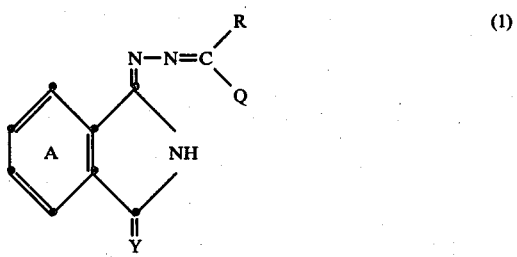

wherein R is hydrogen, alkyl or aryl, Q contains an isocyclic or heterocyclic radical, acyl, carbamoyl or thiocarbamoyl, and Y is the radical of an active methylene group or aromatic amine, which comprises reacting a compound HQ or a hydrazone with an ortho ester or amidine in the presence of a metal donor at elevated temperature in a polar solvent. Pigments made by this process are lightfast and are useful in coloring plastics.

8 Claims, No Drawings

ISOINDOLINE COMPOUNDS AND THE MANUFACTURE AND USE THEREOF

The present invention relates to a process for the manufacture of 1:1 metal complexes of isoindoline azines of the formula

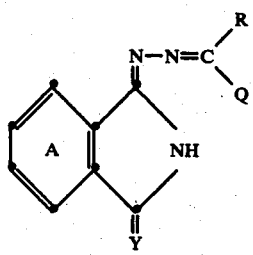
(1)

wherein the ring A can be still further substituted, R is a hydrogen atom, an alkyl or aryl group, and Q is a group of the formula

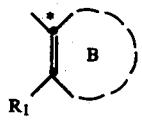
(2)

wherein B is an isocyclic or heterocyclic radical and $R_1$ is a hydroxyl or mercapto group or a radical of the formula

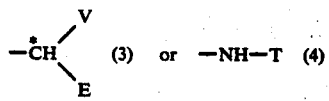

wherein E is a 5- or 6-membered heterocyclic ring which may be fused with benzene nuclei and which contains a nitrogen atom β-oriented to the C* atom, an acyl group, an unsubstituted or a substituted carbamoyl or thiocarbamoyl group, V is an acyl, cyano or nitro group or an unsubstituted or substituted carbamoyl or thiocarbamoyl group, T is a 5- or 6-membered heterocyclic ring which may be fused with benzene nuclei and which contains a nitrogen atom β-oriented to the NH group, or is a radical of the formula

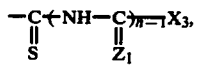

wherein $Z_1$ is an oxygen or a sulfur atom, n is 1 or 2, $X_3$ is an alkyl, cycloalkyl, aralkyl, aryl or heterocyclic radical, or an amino group which is unsubstituted or substituted by an alkyl, cycloalkyl, aralkyl, aryl or heteroaryl radical, and Y is the radical of a compound containing active methylene groups or of an isocyclic or heterocyclic aromatic amine, which process comprises (a) condensing a compound of the formula

H—Q or a hydrazone of the formula

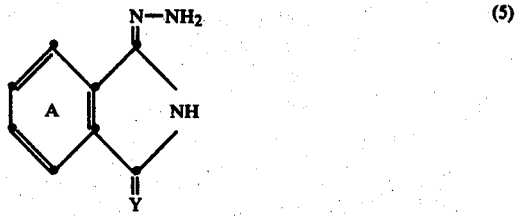

with an ortho-carboxylic acid ester of the formula $$R\text{—}C(OR_2)_3 \qquad (6)$$

wherein R is as defined above and $R_2$ is an alkyl, aralkyl or aryl group, or with an amidine of the formula

wherein R is as defined above, $R_2'$ has the same meaning as $R_2$ or is hydrogen, or with the salt of the amidine of the formula (7) with an organic or inorganic salt, and (b) reacting the condensation product with a compound of the formula (5) or H—Q, in the presence of a metal donor, at elevated temperature and in a polar organic solvent. The isoindolinone azines of the formula (1) can be substituted in the benzene ring A by halogen atoms, for example 2 to 4 chlorine atoms, 1 to 2 alkyl or alkoxy groups, each of 1 to 4 carbon atoms, a phenyl, phenoxy, nitro or benzoylamino group, or an alkanoylamino group of 2 to 6 carbon atoms. Preferably, however, the benzene ring A is unsubstituted.

Y is preferably a radical =N—R'' or a methine radical of the formula

wherein R' is an alkoxycarbonyl, alkylcarbamoyl, carbamoyl, thiocarbamoyl or sulfamoyl group, a benzylcarbamoyl group, a phenylsulfamoyl or phenylsulfonyl group which is unsubstituted or substituted by halogen atoms or alkyl groups of 1 to 4 carbon atoms, but is especially a group of the formula

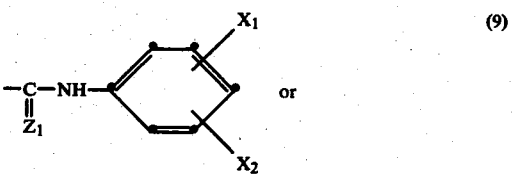

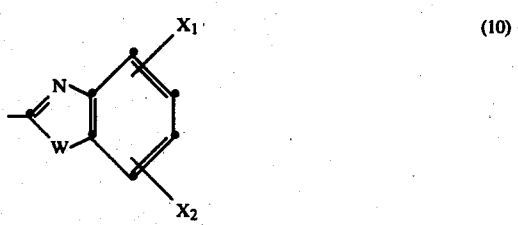

wherein $Z_1$ is an oxygen or a sulfur atom, $X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, benzoylamino, phenylcarbamoyl or phenylsulfamoyl or phenylazo group which is unsubstituted or substituted by chlorine or bromine atoms or methyl groups, and $X_2$ is a hydrogen, chlorine or bromine atom, an alkyl or alkoxy group of 1 to 4 carbon atoms, and W is O, S, or NH. R″ is a radical of the formula (10).

R is e.g. a phenyl or naphthyl radical, but is preferably a hydrogen atom or an alkyl group of 1 to 4 carbon atoms, especially the methyl group.

If Q is a radical of the formula (2), B is e.g. a phenylene or naphthylene radical, especially a 5- or 6-membered heterocyclic ring which may be fused with benzene nuclei and which contains a nitrogen, oxygen or sulfur atom β-oriented to the C* atom and which may contain a further nitrogen atom in the ring and a fused benzene ring and/or a further heterocyclic ring. $R_1$ is preferably a hydroxyl group. Preferred radicals of the formula (2) are:

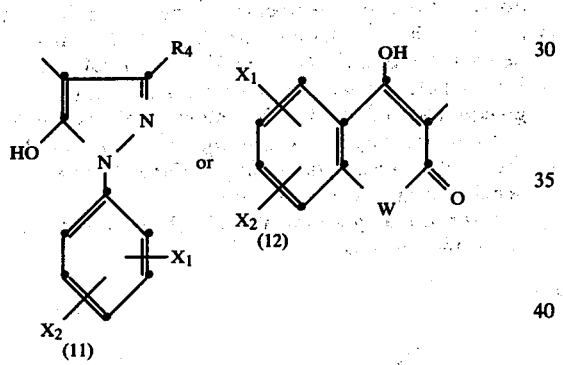

wherein W is O, S or NH, $X_1$ and $X_2$ have the meanings assigned to them above and $R_4$ is alkyl of 1 to 4 carbon atoms, alkoxycarbonyl of 2 to 6 carbon atoms or carbamoyl.

If Q is a radical of the formula

wherein E and V are acyl groups, these groups are preferably acetyl or benzoyl groups. E and V as unsubstituted or substituted carbamoyl or thiocarbamoyl groups are preferably alkylcarbamoyl or alkylthiocarbamoyl groups containing 2 to 6 carbon atoms, benzylcarbamoyl groups, or groups of the formula (9).

E as a 5- or 6-membered heterocyclic ring which may be fused with benzene nuclei is preferably one containing a nitrogen atom β-oriented to the C* atom and N, O or S as further hetero-atom.

Particularly interesting compounds are those of the formula (1), wherein Q is a radical of the formula

wherein $V_1$ is an acetyl, cyano, benzoyl or carbamoyl group, an alkylcarbamoyl group containing 2 to 6 carbon atoms, a benzylcarbamoyl group or a group of the formula

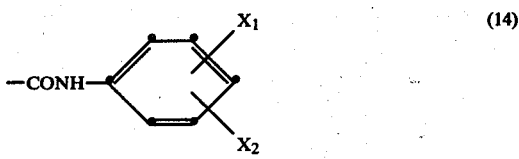

wherein $X_1$ and $X_2$ have the given meanings, $Z_1$ is an oxygen or a sulfur atom and $Z_2$ is the group

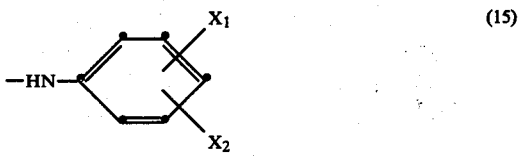

wherein $X_1$ and $X_2$ have the given meanings.

Formula (1) represents only one of the possible isomeric or tautomeric forms.

The starting hydrazones of the formula (5) are known compounds which can be obtained e.g. by the process described in British patent specification No. 1,467,595, by reacting an iminoisoindoline of the formula

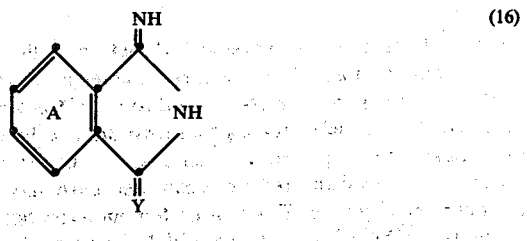

with hydrazine hydrate.

The compounds of the formula (16) are in turn obtained by condensing the corresponding 1-amino-3-iminoisoindolenine with an amine or with a compound containing active methylene groups, especially a compound of the formula $$NCCH_2R'\qquad(17)$$

wherein R′ has the above meaning.

Representative examples are those acetonitriles listed on page 7 of British Pat. No. 1,467,595, as well as cyanoaceto-o-chlorophenyl, -p-chlorophenyl, -m-chlorophenyl, -m-methylphenyl, -p-methylphenyl-, -3,4-dichlorophenyl-, -3,5-dimethylphenyl-, -3,4-dimethylphenyl, -3-chloro-4-methylphenyl-, -o-methoxyphenyl-, -2,4-dimethoxyphenyl-, -2,5-dimethoxyphenyl-, p-acetylamino-phenyl-, p-benzoylaminophenyl-, -3-chloro-4-methyl-, -p-chlorobenzoylaminophenyl-, -4-carbamoylphenyl-, -4-sulfamoylphenyl-, -4-phenylazophenyl-, -4-phenoxyphenyl-, -p-nitrophenyl-, -3-trifluormethylphenyl-, or -2-chloro-5-trifluoromethylphenylamides, 2-cyanomethyl-4-phenyl-, -4-p-nitrophenyl-, -4-fluorophenyl- or -4-methylphenylthiazole.

Suitable compounds containing active methylene groups are also heterocyclic compounds which contain an active methylene group in the heterocyclic ring, for example those listed on pages 7 and 8 of British patent specification No. 1,467,595, e.g. 2,4-dihydroxyquinoline, 1-p-chlorophenyl-3-methyl-5-pyrazolone, 1-p-methylphenyl-3-methyl-5-pyrazolone, 1-phenyl-3-dichlorovinyl-5-pyrazolone, 1-p-methylphenyl-3-dichlorovinyl-5-pyrazolone.

Examples of amines which donate the radical Y are aromatic, but especially heterocyclic, amines, preferably those in which the amino group is located directly at a 5- or 6-membered heterocyclic ring which can contain 1 to 3 nitrogen atoms and, in addition, oxygen and sulfur atoms. An unsubstituted or substituted benzene nucleus can be fused to the heterocyclic parent nucleus. Examples of such amines are those listed on pages 6 to 7 of British patent specification No. 1,467,595, and, in addition, 2-aminopyridine, diaminophthalazine, 2-amino-4-hydroxyquinoline, 2,6-diaminopyridine, 2-amino-4,5-dimethylthiazole.

In the compound H—Q, Q is e.g. the radical of the formula (2), wherein $R_1$ is preferably a hydroxyl group and B is preferably a naphthalene radical or a 5- or 6-membered heterocyclic ring which contains an oxygen, a sulfur or, preferably, a nitrogen atom $\beta$-oriented to the C* atom and which may contain a further nitrogen atom in the ring and a fused benzene ring and/or a further heterocyclic ring.

Representative isocyclic hydroxy compounds are those of the formula

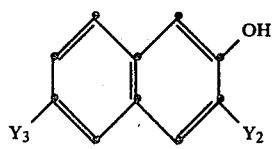

(18)

wherein $Y_2$ is a hydrogen atom, a carboxyl or carbamoyl group, an alkoxycarbonyl or alkylcarbamoyl group containing 2 to 6 carbon atoms, a phenylcarbamoyl group which is unsubstituted or substituted in the phenyl moiety by halogen atoms or alkyl or alkoxy groups of 1 to 4 carbon atoms, and $Y_3$ is a hydrogen or halogen atom, or a methoxy, nitro or cyano group.

Examples of isocyclic hydroxy compounds are: 2-naphthol, 6-bromo-2-naphthol, 6-nitro-2-naphthol, 2,3-hydroxynaphthoic acid, 2-hydroxy-3-naphthoanilide, 2-hydroxy-6-bromo-3-naphthoanilide. Exemplary of a cycloaliphatic compound which contains active methylene groups is 5,5-dimethylcyclohexane-1,3-dione (Dimedon).

Heterocyclic hydroxy compounds are preferred, for example the compounds of the formula

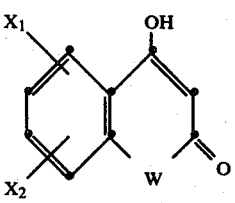

(19)

wherein $X_1$, $X_2$ and W have the above meanings, and those of the formula

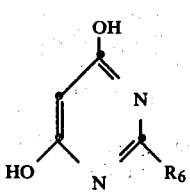

(21)

wherein $R_6$ is a hydrogen atom, an alkyl group of 1 to 4 carbon atoms, a phenyl or hydroxyl group, or those of the formula

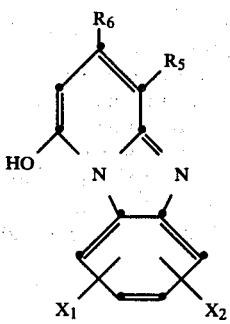

(22)

wherein $X_1$, $X_2$ and $R_6$ have the above meanings, and $R_5$ is a cyano group, an alkoxycarbonyl group of 2 to 6 carbon atoms or a carbamoyl group, or those of the formula

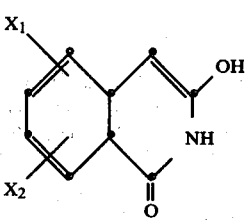

(23)

wherein $X_1$ and $X_2$ have the given meanings, and, finally, pyrazoles of the formula

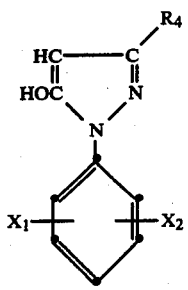

(24)

wherein $R_4$, $X_1$ and $X_2$ have the above meanings.

Representative examples are:
2,4-dihydroxyquinoline
2,4-dihydroxy-5,6,7 or 8-chloroquinoline
2,4-dihydroxy-6,8- or 7,8-dichloroquinoline
2,4-dihydroxy-6,7 or 8-methylquinoline
2,4-dihydroxy-6-chloro-8-methylquinoline
2-methyl-4-hydroxyquinoline
2-methyl-4-hydroxy-6-chloroquinoline
2-methyl-4-hydroxy-6-methoxyquinoline
3-hydroxyisoquinoline
barbituric acid
2-methyl-4,6-dihydroxypyrimidine
4-hydroxycoumarin
4-hydroxy-6-methylcoumarin
4-hydroxy-6-methoxycoumarin
4-hydroxy-6-chlorocoumarin
4-hydroxy-6-chloro-5,7-dimethylcoumarin
1-phenyl-3-methylpyrazol-5-one
1-phenyl-3-carboxypyrazol-5-one
1-phenyl-3-carbamoylpyrazol-5-one
1-phenyl-3-methoxycarbonylpyrazol-5-one
1-phenyl-3-ethoxycarbonylpyrazol-5-one
1-o-chlorophenyl-3-methylpyrazol-5-one
1-p-chlorophenyl-3-methylpyrazol-5-one
1-o-methylphenyl-3-methylpyrazol-5-one
1-p-methylphenyl-3-methylpyrazol-5-one.

Preferred compounds H—Q are the compounds of the formula

(25)

and, in particular, those of the formula

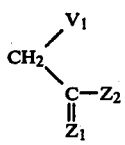

(26)

wherein V, $V_1$, E, $Z_1$ und $Z_2$ are as defined above.

Examples of compounds of the formula (26) are the substituted acetonitriles listed on page 7 of British Pat. No. 1,467,595, and also
acetoacetylaniline
acetoacetyl-p-chloroaniline
acetoacetyl-o-methoxyaniline
acetoacetyl-2,5-dimethoxy-4-chloroaniline
2-acetoacetylaminobenzimidazole
thiocarbamoylacetonitrile
N-phenylthiocarbamoylacetonitrile
N-p-chlorophenylthiocarbamoylacetonitrile
N-p-tolylthiocarbamoylacetonitrile
N-p-acetylaminophenylthiocarbamoylacetonitrile
N-m-trifluoromethylphenylthiocarbamoylacetonitrile
N-p-phenoxyphenylthiocarbamoylacetonitrile
N-p-nitrophenylthiocarbamoylacetonitrile
N-α-naphthylthiocarbamoylacetonitrile
N-p-methoxyphenylthiocarbamoylacetonitrile
thioacetylacetone
thioacetoacetonilide
N-cyclohexylthiocarbamoylacetonitrile
cyanoacetamide
cyanoaceto-N-methylamide
cyanoaceto-p-chloroanilide
acetylacetophenone
cyanoacetophenone
2-cyanomethylbenzimidazole
2-cyanomethylquinazol-4-one.

If Q is the radical of the formula (4), $H_2NT$ can either be a heterocyclic amine or a thiocarbamoyl derivative.

Preferred heterocyclic amines of the formula $H_2NT$ are those in which the amino group is located at a 5- or 6-membered heterocyclic ring which contains a nitrogen atom β-oriented to the amino group and may contain N,O or S as further hetero-atom and which can be fused through benzene rings. Representative heterocyclic amines are the amines listed on pages 6–7 of British Pat. No. 1,467,595, and also 3-aminoisoindolenin-1-one, 1-amino-4-chlorophthalazine or 1,4-diaminophthalazine and the imine forms thereof.

Preferred thiocarbamoyl derivatives of the formula $H_2NT$ are those in which T is the radical of the formula

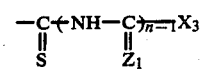

wherein $Z_1$ and n have the given meanings and $X_3$ is an amino group which is substituted by a heteroaryl or aryl radical of the formula

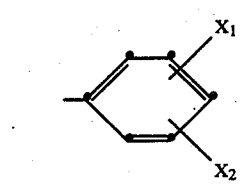

wherein $X_1$ and $X_2$ have the given meanings.

As ortho-carboxylic acid esters of amidines of the formulae (6) and (7) it is preferred to use those in which $R_2$ is alkyl of 1 to 4 carbon atoms and $R_2'$ is alkyl of 1 to 4 carbon atoms or phenyl.

As metal donors it is preferred to use the salts of zinc, cadmium, manganese, cobalt, iron, and especially of copper and nickel, and mixtures of such metals. It is preferred to use the formates, acetates or stearates of these metals.

The reaction of the components can be carried out in varying sequence. It is preferred to condense the hydrazone of the formula (5) with the ortho-carboxylic acid ester of the formula (6) or the amidine of the formula (7) to give the azine of the formula

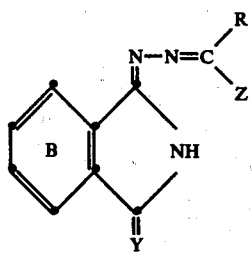

(27)

wherein Z is a group —OR₂ or —NHR₂', in which R₂ and R₂' have the given meanings, and to react the latter with the compound H—Q in the presence of the metal donor.

One variant of the process consists in condensing the compound H—Q with the ortho-carboxylic acid ester of the formula (6) or an amidine of the formula (7) in the presence of the metal donor, and reacting the condensation product with the hydrazone of the formula (5).

The reaction of the hydrazone (5) with the ortho-carboxylic acid ester is preferably carried out in an excess of this latter, and the other reactions are carried out in a polar organic solvent, especially a hydrophilic polar solvent, for example an amide such as dimethyl formamide, dimethyl acetamide or N-methylpyrrolidone, as well as dimethyl sulfoxide, acetonitrile or an alcohol, e.g. ethyl cellosolve. A mixture of polar solvents can also be used.

The reaction temperature is advantageously in the range from 100°–200° C.

The metal complex is isolated in conventional manner by filtration. The filter cake is washed thoroughly with solvent. The product is obtained in excellent yield and purity and can be used, without further purification, in finely dispersed form for coloring organic material of high molecular weight, e.g. cellulose ethers and esters, such as ethyl cellulose, acetyl cellulose, nitrocellulose, polyamide and polyurethanes, or polyesters, natural resins or synthetic resins, e.g. aminoplasts, especially urea-formaldehyde and melamineformaldehyde resins, alkyd resins, phenolic plastics, polycarbonates, polyolefins such as polystyrene, polyvinyl chloride, polyethylene, polypropylene, polyacrylonitrile, polyacrylates, thermoplastics or curable acrylic resins, rubber, casein, silicone and silicone resins, singly or in mixtures. The specified materials of high molecular weight can be in the form of plastics, melts or of spinning solutions, lacquers, or printing inks. Depending on the end-use, it is advantageous to use the pigments of the present invention as toners or in the form of preparations.

The pigment can be used in the form in which it is obtained in the synthesis or in slightly ground form to give opaque colorations. However, it can also be more thoroughly ground to give transparent colorations, for example strong metal effect finishes.

Mill base formulations in lacquers have advantageous flow properties.

The colorations obtained e.g. in plastics, filaments and lacquers, have high colour strength, excellent purity of shade, good dispersibility, good fastness to overspraying, migration, heat, light and migration as well as good gloss.

The manufacture of 1:1 metal complexes of azines of the formula

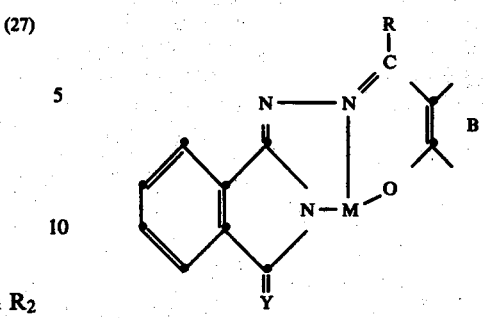

by condensing the corresponding hydrazono-isoindoline with an oxo compound of the formula

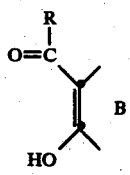

and subsequent metalation, is described in British Pat. No. 1,467,595. Compared with this prior art process, the process of the present invention constitutes a simplified procedure.

The invention is illustrated by the following Examples, in which percentages are by weight.

EXAMPLE 1

(a) 11.6 g (0.06 mole) of 75% 1,3-diiminoisoindoline and 11.7 g (0.06 mole) of cyanoaceto-p-chloroanilide are dissolved in 50 ml of dimethyl formamide and 3.6 ml (0.06 mole) of glacial acetic acid and the solution is stirred overnight at room temperature. Complete reaction to 1-(cyano-p-chlorophenylcarbamoylmethylene)-3-iminoisoindoline is confirmed next day by thin-layer chromatography. Then 3.1 ml of hydrazone hydrate (0.06 mole) are added dropwise at room temperature and in the course of 1 to 2 minutes to the resultant suspension. The mixture is stirred at room temperature for 45 minutes. Subsequent analysis by thin-layer chromatography confirms that the 1-(cyano-p-chlorophenylcarbamoylmethylene)-3-iminoisoindoline is completely reacted. 250 ml of ethanol are then added to the mixture, which is thoroughly stirred at room temperature for 15–20 minutes. The precipitate is collected by filtration, washed with a small amount of ethanol and dried overnight in vacuo at 50°–60° C., affording 16.8 g (83% of theory) of the compound of the formula

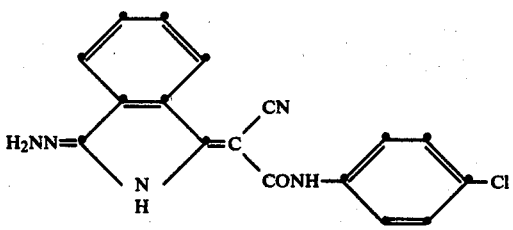

in the form of a yellowish brown powder.

(b) 1 drop of concentrated sulfuric acid is added to 25 ml of triethyl orthoformate and the mixture is heated to 140° C. With stirring, 3.4 g (0.01 mole) of the compound obtained in (a) are added in portions at the same temperature. The mixture is allowed to react for 1 hour at 140° C., while simultaneously distilling off alcohol. The mixture is then cooled to 80° C. and filtered. The filter cake is washed with alcohol and dried overnight in vacuo at 80° C., affording 3.54 g (90% of theory) of the compound of the formula

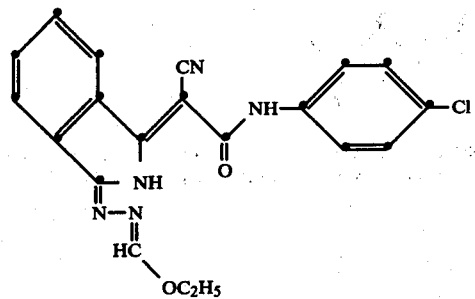

in the form of an orange powder.

Microanalysis: C$_{20}$H$_{16}$N$_5$O$_2$Cl mol. wt. 393.83 found: 61.00% C, 4.10% H, 17.79% N, 9.00% Cl; calculated: 61.00% C, 4.3% H, 17.8% N, 9.0% Cl.

EXAMPLE 2

1 drop of conc. sulfuric acid is added to 40 ml of triethyl orthoacetate and the mixture is heated to 130°–135° C. Then 6.75 g (0.02 mole) of the compound obtained in Example (1a) are added in portions at the same temperature in the course of 30 minutes. The reaction is allowed to go to completion for 1 hour at 140° C. and the mixture is then cooled to 80° C. and filtered. The filter cake is washed with alcohol and dried in vacuo at 80° C., affording 6.95 g (85% of theory) of the compound of the formula

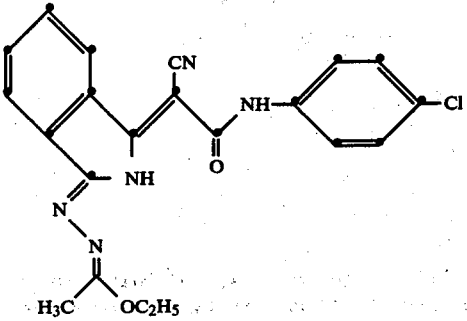

in the form of an orange powder.

Microanalysis: C$_{21}$H$_{18}$N$_5$O$_2$Cl mol. wt. 407.86 calculated: 61.84% C, 4.45% H, 17.17% N, 8.69% Cl; found: 61.4% C, 4.2% H, 17.8% N, 9.1% Cl.

In accordance with the procedure of Example 1 or 2, a hydrazone of the formula

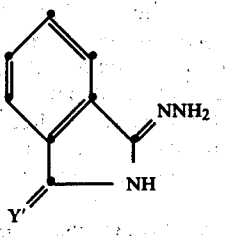

is reacted with an ortho-carboxylic acid ester of the formula

R$_1'$—C(OR$_3''$)$_3$ to give compounds of the formula

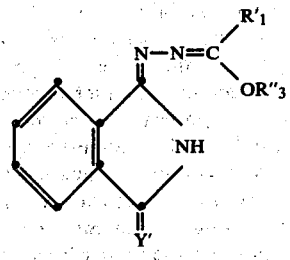

wherein Y', R$_1'$ and R$_3''$ have the meanings given in Table 1.

TABLE 1

| Example | Y' | R'$_1$ | R''$_3$ |
|---|---|---|---|
| 3 | NC—CCON—⟨⟩—NO$_2$ (with ‖ and H) | —H | —C$_2$H$_5$ |
| 4 | NC—CCON—⟨⟩—NO$_2$ (with ‖ and H) | CH$_3$ | —C$_2$H$_5$ |
| 5 | NC—CCON—⟨⟩—N=N—⟨⟩ (with ‖ and H) | —H | —CH$_3$ |

TABLE 1-continued

| Example | Y' | R'₁ | R"₃ |
|---|---|---|---|
| 6 | NC—C(=O)—CONH—C₆H₄—O—C₆H₅ | —H | —CH₃ |
| 7 | NC—C(=O)—CONH—C₆H₄—NHCOCH₃ | —H | —C₂H₅ |
| 8 | NC—C(=O)—CONH—C₆H₄—CH₃ | —CH₃ | —C₂H₅ |
| 9 | CN—C(=O)—CONH—C₆H₄—OCH₃ | —CH₃ | —CH₃ |
| 10 | NCC(=O)—CONH—C₆H₃(CH₃)(Cl) | —H | —C₂H₅ |
| 11 | NC—C(=O)—CONH—C₆H₃(CF₃)(Cl) | —H | —C₂H₅ |
| 12 | NC—C(=O)—CONH—C₆H₃(Cl)(Cl) | —CH₃ | —C₂H₅ |
| 13 | NC—C(=O)—CONH—C₆H₄—NHCO—C₆H₅ | —H | —C₂H₅ |
| 14 | NC—C(=O)—CONH—C₆H₄—CONH₂ | —CH₃ | —C₂H₅ |
| 15 | NC—C(=O)—CONH—C₆H₄—SO₂NH₂ | —CH₃ | —C₂H₅ |
| 16 | NC—C(=O)—CONH—C₆H₄—CF₃ | —CH₃ | —C₂H₅ |
| 17 | NC—C—(benzimidazole) | —H | —C₂H₅ |
| 18 | NC—C—(benzothiazole) | —H | —CH₃ |

TABLE 1-continued

| Example | Y' | R'₁ | R''₃ |
|---|---|---|---|
| 19 | NC-C(=)-benzoxazol-2-yl | —H | —$C_2H_5$ |
| 20 | 1H-benzimidazol-2-yl=N— | —H | —$C_2H_5$ |
| 21 | benzothiazol-2-yl=N— | —H | —$C_2H_5$ |
| 22 | benzoxazol-2-yl=N— | —H | —$C_2H_5$ |
| 23 | (4-chloro-phthalazin-1-yl)=N— | —H | —$C_2H_5$ |
| 24 | NC—C(=)—(4-oxo-3H-quinazolin-2-yl) | —H | —$C_2H_5$ |
| 25 | NC—C(=)—COO$C_2H_5$ | —H | —$C_2H_5$ |
| 26 | NC—C(=)—CONH$C_2H_5$ | —H | —$C_2H_5$ |
| 27 | NC—C(=)—CONH—C₆H₄—Cl | —H | —C₅H₅ (cyclopentadienyl) |
| 28 | NC—C(=O)—CONH—C₆H₄—Cl | —H | —$C_4H_9$ |
| 29 | NC—C(=O)—CONH—C₆H₄—Cl | —H | —$CH_2$—C₅H₅ |

EXAMPLE 30

1.97 g (0.005 mole) of the compound obtained in Example (1b) and 1.31 g (0.0052 mole) of nickel acetate tetrahydrate are suspended in 35 ml of dimethyl formamide and the mixture is heated to 60° C. Then 1.05 g (0.005 mole) of 1-p-chlorophenyl-3-methyl-5-pyrazolone are added and the mixture is further heated to 115° C. The reaction is allowed to go to completion for 1½ hours at the same temperature, then the mixture is cooled to 80° C. and filtered. The filter cake is washed with dimethyl formamide and alcohol and dried in vacuo at 80° C., affording 2.3 g (75% of theory) of the 1:1 nickel complex of the formula

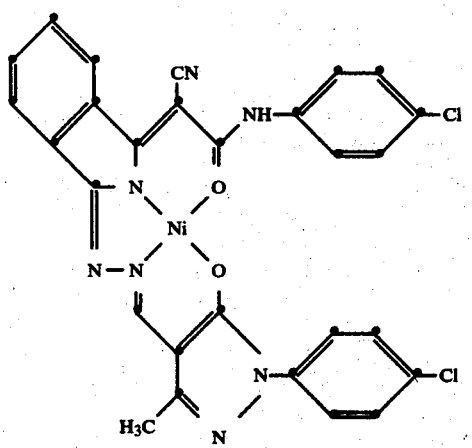

Microanalysis: $C_{28}H_{17}Cl_2N_7O_2Ni$ mol. wt. 613.1 calculated: 54.80% C, 2.77% H, 11.58% Cl, 15.98% N, 9.57% Ni; found: 54.5% C, 2.9% H, 11.4% Cl, 16.2% N, 9.8% Ni.

The above metal complex pigment colors plastics in pure scarlet shades of excellent fastness properties.

EXAMPLE 31

The procedure of Example 30 is repeated using 5,5-dimethyl-1,3-cyclohexanedione instead of 1-p-chlorophenyl-3-methyl-5-pyrazolone. Working up gives a 1:1 nickel complex (65% of theory) of the formula

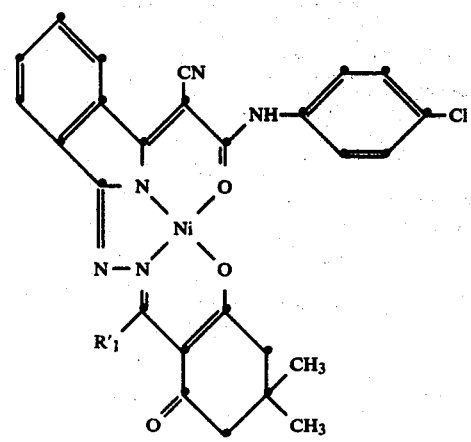

$R_1'=H$

Microanalysis: $C_{26}H_{20}ClN_5O_3Ni$ mol. wt. 544.6 calculated: 57.34% C, 3.7% H, 12.86% Cl, 6.5% N, 10.78% Ni; found: 57.1% C, 3.8% H, 13.1% Cl, 6.4% N, 10.9% Ni.

This nickel complex colors plastics in pure orange shades of excellent fastness properties.

EXAMPLE 32

The procedure of Example 31 is repeated, using the compound obtained in Example 2 instead of that obtained in Example (1b), to give also a pure orange metal complex of the formula of Example 31 ($R_1'=CH_3$).

EXAMPLE 33

3.03 g (0.01 mole) of the compound of the formula

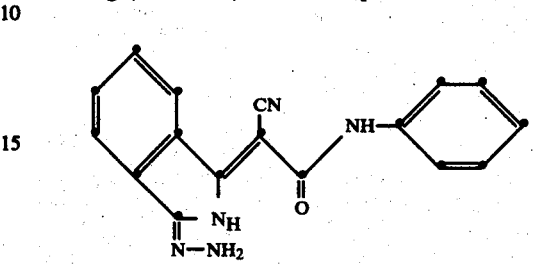

(obtained from hydrazine hydrate and 1-(cyanophenyl-carbamoylmethylene)-3-iminoisoindoline) are suspended in 40 ml of dimethyl formamide. Then 2 ml (0.012 mole) of triethyl orthoformate are added and the reaction mixture is heated to 80° C. and stirred for 10 minutes at the same temperature. A warm solution (80° C.) of 2.08 g (0.01 mole) of 1-p-chlorophenyl-3-methyl-5-pyrazolone and 2.6 g (0.0105 mole) of nickel acetate tetrahydrate in 25 ml of dimethyl formamide is then added to the mixture, which is heated to 115° C. After a reaction time of 2-3 hours at the same temperature, the mixture is cooled to 80° C. and filtered. The filter cake is washed with dimethyl formamide and alcohol and dried overnight in vacuo at 80° C., affording 4.7 g (81% of theory) of the 1:1 nickel complex of the composition $C_{28}H_{18}ClN_7O_2Ni$ and having the formula

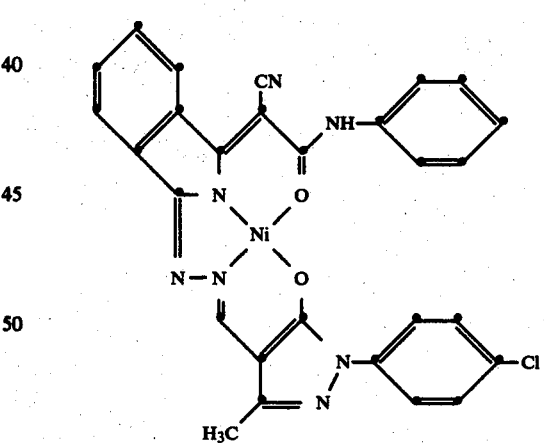

Microanalysis: $C_{28}H_{18}ClN_7O_2Ni$ mol. wt. 578.66 *calculated: 57.9% C, 3.14% H, 16.9% N, 6.1% Cl, 10.1% Ni; found: 57.4% C, 3.3% H, 17.0% N, 6.1% Cl, 10.4% Ni.

*taking into account the 0.3% of water found.

EXAMPLE 34

2.08 g (0.01 mole) of 1-p-chlorophenyl-3-methyl-5-pyrazolone are suspended in 40 ml of dimethyl formamide. After addition of 2 ml (0.012 mole) of triethyl orthoformate, the mixture is heated to 80° C. and stirred for 10 minutes at this temperature. Then 2.6 g (0.0105 mole) of nickel acetate tetrahydrate are added and stirring is continued for 5 minutes at 80° C. Then 3.03 g (0.01 mole) of the 1-(cyanophenylcarbamoylmethylene)-3-hydrazinoisoindoline of the formula

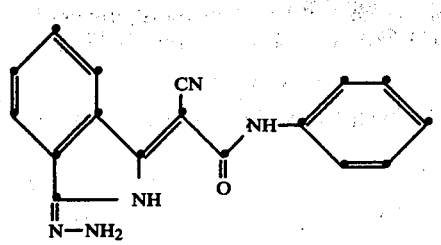

are added and the reaction mixture is heated to 115° C. and stirred for 2½ hours at this temperature, then cooled to 80° C. The pigment is isolated by filtration and dried overnight in vacuo at 80° C., affording 3.05 g (53% of theory) of a 1:1 nickel complex pigment which is identical with the product of Example 33.

EXAMPLES 35–49

Table 2 lists further nickel complexes of the formula

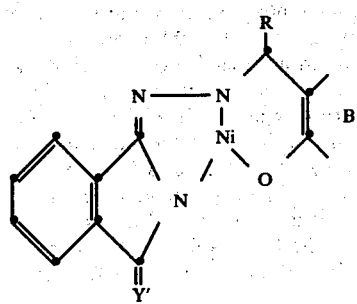

(for simplicity's sake only one of the possible isomeric or tautomeric forms is indicated) which are obtained substantially in accordance with the procedure of Example 30 or 33 either by condensing the reaction mixture of a hydrazone of the formula

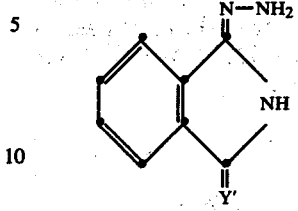

with triethyl orthoformate or triethyl orthoacetate, or the azine of the formula

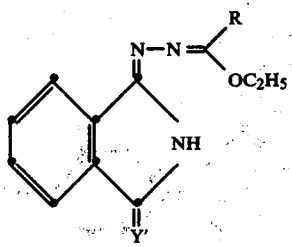

in the presence of nickel acetate tetrahydrate, with a compound of the formula

which contains active methylene groups, in which formulae Y', R, V and E have the meanings given in columns 2, 3, 4 and 5 respectively. Column 6 indicates the shade obtained in polyvinyl chloride.

TABLE 2

| Example | Y' | R | V | E | Shade in PVC |
|---|---|---|---|---|---|
| 35 | NC—C(=O)—CON(H)—⟨phenyl⟩—N=N—⟨phenyl⟩ | H | acetyl | phenyl-amino | red |
| 36 | NH—C(=O)—CON(H)—⟨phenyl⟩—Cl | H | cyano | p-chloro-phenyl-amino | red |
| 37 | NC—C(=O)—CON(H)—⟨phenyl⟩—Cl | H | p-methyl-phenyl-carbamoyl | p-methyl-phenyl-amino | red |
| 38 | NC—C(=O)—CON(H)—⟨phenyl⟩—Cl | H | acetyl | phenyl-amino | red |
| 39 | NC—C(=O)—CON(H)—⟨phenyl⟩—Cl | H | 2-benz-imidazolyl | methyl | claret |
| 40 | NC—C(=O)—CONH—⟨phenyl with Cl, Cl⟩ | H | cyano | amino | orange |

TABLE 2-continued

| Example | Y' | R | V | E | Shade in PVC |
|---|---|---|---|---|---|
| 41 | NC—C(=)—CONH—C₆H₃(Cl)₂ | H | cyano | methyl-amino | orange |
| 42 | NC—C(=)—CONH—C₆H₄—Cl | H | cyano | benzyl-amino | orange |
| 43 | NC—C(=)—CONH—C₆H₅ | H | acetyl | phenyl | orange |
| 44 | NC—C(=)—CONH—C₆H₃(Cl)₂ | H | cyano | phenyl | orange |
| 45 | 2-benzimidazolylimino | H | cyano | p-chloro-phenyl-amino | orange |
| 46 | 2-benzthiazolylimino | H | cyano | p-chloro-phenyl-amino | red |
| 47 | 2-benzoxazolylimino | H | cyano | p-chloro-phenyl amino | orange |
| 48 | NC—C(2-benzimidazolyl) | H | cyano | phenyl-amino | red |
| 49 | NC—C(2-benzothiazolyl) | H | cyano | phenyl-amino | red |

EXAMPLE 50

2.36 g (0.006 mole) of the compound prepared in Example 1b) and 1.57 g (0.0068 mole) of nickel acetate tetrahydrate are heated in 40 ml of N-methylpyrrolidone to about 80° C. Then 1.06 g (0.006 mole) of cyanoacetothioanilide are added and the reaction is allowed to go to completion for 1½ hours at 145° C. The reaction mixture is then cooled to 80° C. and filtered. The filter cake is washed with dimethyl formamide and alcohol and dried overnight in vacuo at 80° C., affording 2.22 g (64% of theory) of a red 1:1 nickel complex of the formula

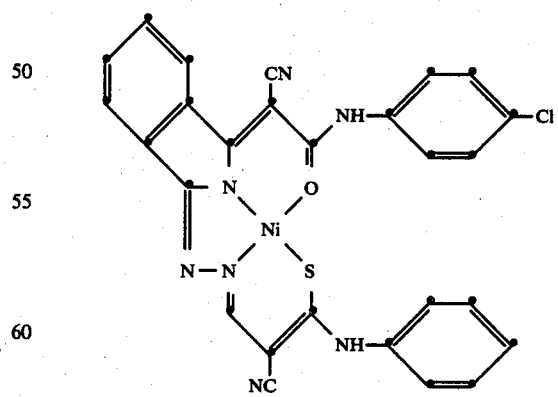

which has excellent fastness properties.

Microanalysis: $C_{27}H_{16}ClN_7OSNi$ mol. wt. 580.7 calculated: 55.85% C, 2.78% H, 16.88% N, 5.52% S, 6.11% Cl, 10.11% Ni; found: 55.1% C, 3.1% H, 16.4% N, 5.5% S, 5.8% Cl, 9.6% Ni.

EXAMPLES 51–55

Table 3 lists further nickel complexes of the formula

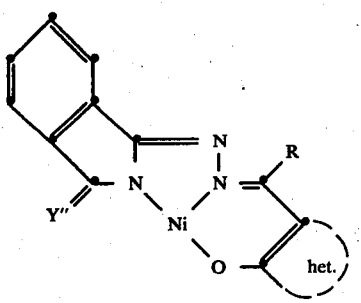

(only one of the possible isomeric or tautomeric forms is indicated) which are obtained substantially in accordance with Example 30 or 33 by condensing the azine of the formula

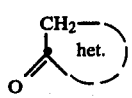

in the presence of nickel acetate tetrahydrate, with a heterocyclic compound of the formula $$\underset{O}{\overset{CH_2-}{\diagup}}\!\!\left(\!het.\right)$$

which contains active methylene groups, in which formulae Y″, R, Z and $$\underset{O}{\overset{CH_2-}{\diagup}}\!\!\left(\!het.\right)$$

have the meanings given in columns 2, 3, 4 and 5 respectively. Th shade obtained in PVC is indicated in column 6.

TABLE 3

| Example | Y″ | R | Z | $\underset{O}{\overset{H_2C-}{\diagup}}\!\!\left(\!het.\right)$ | Shade in PVC |
|---|---|---|---|---|---|
| 51 | NC—C(=O)—CONH—⟨C₆H₄⟩—Cl | H H | —NC₃H₇ | [pyrazolone with CH₃, H₂C, N–N, phenyl-Cl] | red |
| 52 | ″ | H | —NH—⟨C₆H₅⟩ | ″ | red |
| 53 | ″ | H | OC₂H₅ | [barbiturate-type ring with H₂C, NH, N–H, 3×C=O] | yellow |

TABLE 3-continued

| Example | Y'' | R | Z | ![structure](H2C-het/O) | Shade in PVC |
|---|---|---|---|---|---|
| 54 | " | H | OC₂H₅ | (structure with H₂C-C(=O) on benzene ring ortho to NH) | red |
| 55 | " | H | OC₂H₅ | (structure with H₂C-C(=O) on benzene ring ortho to NH) | violet |

EXAMPLE 56

2.36 g (0.006 mole) of the compound obtained in Example 1b) and 1.57 g (0.0063 mole) of nickel acetate tetrahydrate are suspended in 40 ml of N-methylpyrrolidone. After addition of 0.94 g (0.006 mole) of benzimidazolylacetonitrile, the mixture is heated to 140° C. and stirred at the same temperature for 1½ hours, then cooled to 50° C. and filtered. The filter cake is washed with dimethyl formamide and alcohol and dried at 80° C. in vacuo, affording 2.2 g (63% of theory) of a 1:1 nickel complex pigment of the formula

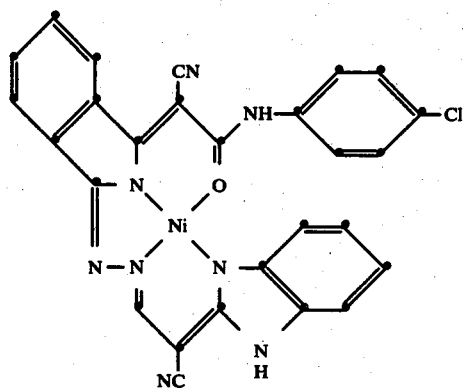

which colors plastics in claret shades of excellent fastness properties.

Microanalysis: C₂₇H₁₅ClN₈ONi mol. wt. 561.6 calculated: 57.74% C, 2.69% H, 19.95% N, 6.31% Cl, 10.45% Ni; found: 57.5% C, 3.0% H, 20.0% N, 6.1% Cl, 10.6% Ni.

EXAMPLE 57

1.97 g (0.005 mole) of the compound obtained in Example 1b) and 1.31 g (0.00525 mole) of nickel acetate are suspended in 40 ml of N-methylpyrrolidone and the mixture is heated to 80° C. Then 0.73 g (0.005 mole) of 1-imino-3-isoindolinone are added and the reaction is allowed to go to completion for 1½ hours at 145° C. The reaction mixture is then cooled to 80° C. and filtered. The filter cake is washed with dimethyl formamide and alcohol and dried overnight at 80° C. in vacuo, affording 1.62 g (63% of theory) of a 1:1 nickel complex of the formula

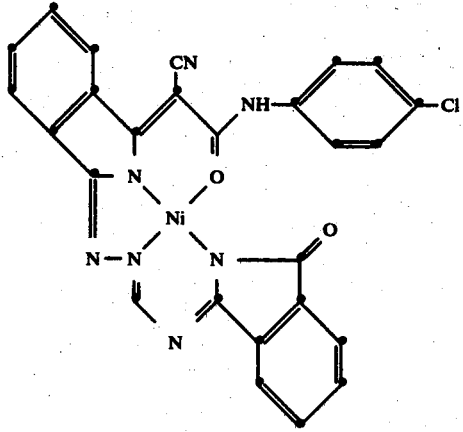

Microanalysis: C₂₆H₁₄ClN₇O₂Ni mol. wt. 515.16 calculated: 56.72% C, 2.56% H, 17.81% N, 6.44% Cl, 10.66% Ni; found: 56.0% C, 2.7% H, 17.5% N, 6.4% Cl, 10.9% Ni.

This complex colors plastics in pure scarlet shades of excellent fastness properties.

EXAMPLES 58–66

Table 4 lists further nickel complexes of the formula

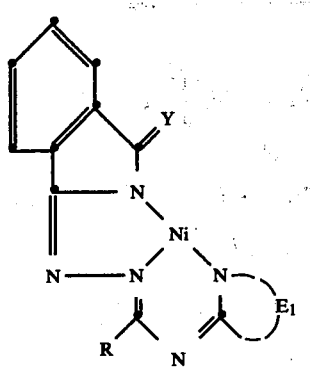

(for simplicity's sake only one of the possible isomeric or tautomeric forms is indicated) which are obtained in accordance with the procedure of Example 57 by condensing an azine of the formula

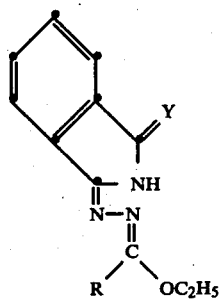

in the presence of nickel acetate tetrahydrate, with an amine of the formula R'NH$_2$, in which formulae Y, R' and R have the meanings given in columns 2, 3 and 4 respectively. The shade obtained in polyvinyl chloride is indicated in column 6.

TABLE 4

| Example | Y | R'NH$_2$ | R | Shade in PVC |
|---|---|---|---|---|
| 58 | NC–C=CONH–(4-Cl-phenyl) | 1-amino-4-chloro-phthalazine | H | red |
| 59 | " | 2-amino-benzimidazole | H | red |
| 60 | " | 2-amino-benzimidazole | CH$_3$ | red |
| 61 | " | 3-amino-indazole | H | red |
| 62 | " | 3-aminoiso-indoleninone (3-imino-isoindolinone) | H | red |
| 63 | " | 2-amino-benzimidazole | CH$_3$ | red |
| 64 | " | 1,4-diamino-phthalazine | H | orange |
| 65 | 2-benzthiazolyl-imino | 3-amino-iso-indoleninone | H | orange |
| 66 | 2-benzimidazolyl-imino | 2-amino-benzimidazole | H | orange |

EXAMPLE 67

2.2 g (0.011 mole) of N,N'-diphenylformamidine and 3.4 g (0.01 mole) of the compound obtained in Example 1a) are suspended in 25 ml of dimethyl formamide. The mixture is heated to 135°–140° C. and stirred for 1 hour at the same temperature, then cooled to room temperature. After addition of 80 ml of alcohol the mixture is stirred thoroughly for 15 minutes at room temperature. The precipitate is collected by filtration, washed with a small amount of alcohol and dried overnight at 50°–60° C. in vacuo, affording 3.3 g (75% of theory) of the compound of the formula

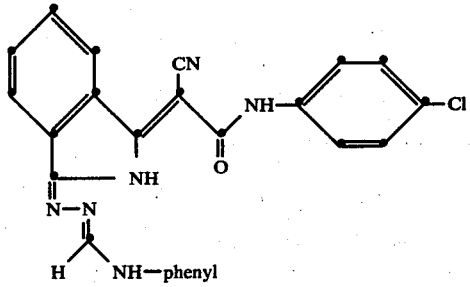

in the form of a yellow orange powder.

Microanalysis: C$_{24}$H$_{17}$N$_6$OCl mol. wt. 440.5 found: 65.6% C, 3.9% H, 19.2% N, 7.9% Cl; calculated: 65.38% C, 3.85% H, 19.06% N, 8.05% Cl.

EXAMPLE 68

The procedure of Example 67 is repeated, using N,N'-di-n-propylformamidine instead of N,N'-diphenylformamidine. Working up affords the compound of the formula

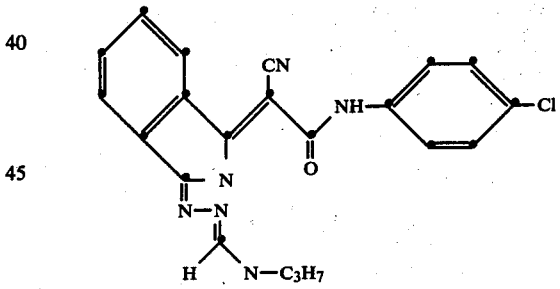

EXAMPLE 69

The procedure of Example 33 is repeated, using the corresponding amount of N,N'-dipropylformamidine instead of triethyl orthoformate. The same red 1:1 nickel complex is obtained as in Example 33.

EXAMPLE 70

1.25 g (0.005 mole) of nickel acetate tetrahydrate and 1.96 g (0.005 mole) of the compound obtained in Example 1b) are suspended in 40 ml of dimethyl formamide and the mixture is heated to 115°–120° C. After 5 minutes reaction time at this temperature the mixture is cooled to 40° C. and, after addition of 0.69 g (0.005 mole) of thiobenzamide, slowly heated to 100°–105° C. The reaction is allowed to go to completion for 1 hour at the same temperature, then the mixture is cooled to 70° C. and filtered. The filter cake is washed with dimethyl formamide and ethanol and dried overnight at 80° C. in vacuo, affording 1.7 g (61% of theory) of the compound of the formula

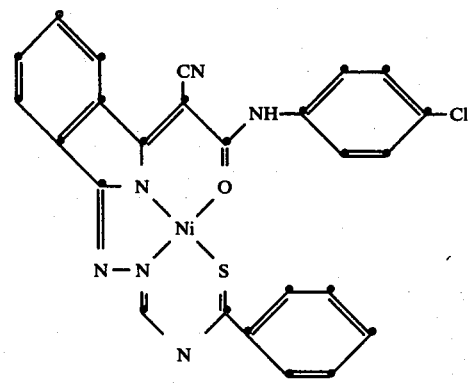

in the form of a red powder.

Microanalysis: $C_{25}H_{15}ClN_6OSN$ mol. wt. 541.6 calculated: 55.44% C, 2.79% H, 15.52% N, 5.92% S, 6.55% Cl, 10.84% Ni; found: 55.4% C, 3.1% H, 16.0% N, 5.5% S, 6.7% Cl, 10.7% Ni.

This complex colors plastics and lacquers in red shades of excellent fastness properties.

EXAMPLES 71–83

Table 5 lists further nickel complexes of the formula

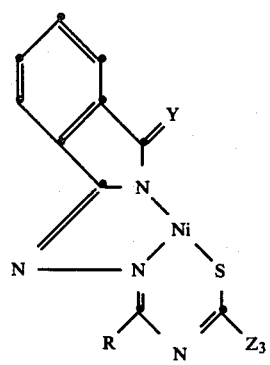

(for simplicity's sake only one of the possible isomeric or tautomeric forms is indicated) which are obtained substantially in accordance with the procedure of Example 70 by condensing an azine of the formula

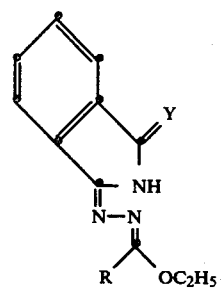

in the presence of nickel acetate tetrahydrate, with a thiocarbamoyl derivative of the formula

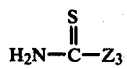

in which formulae Y, R and $Z_3$ have the meanings given in columns 2, 3, and 4 respectively. The shade obtained in polyvinyl chloride is indicated in column 5.

TABLE 5

| Example | R | $Z_3$ | Shade in PVC |
|---|---|---|---|
| 71 | H | —⟨phenyl⟩—Cl | red |
| 72 | CH₃ | " | red |
| 73 | H | —CH₃ | yellow |
| 74 | H | —NH₂ | claret |
| 75 | H | —NHCO—⟨phenyl⟩ | red |
| 76 | CH₃ | " | claret |
| 77 | H | —NH—⟨phenyl⟩ | red |
| 78 | H | —NH—⟨naphthyl⟩ | red |
| 79 | H | —NH—⟨pyridyl⟩ | red |
| 80 | H | —NH—⟨phenyl⟩—CH₃ | red |
| 81 | H | —NH—⟨phenyl⟩—OCH₃ | red |
| 82 | H | —NH—⟨phenyl⟩—Cl | red |
| 83 | H | —NH—⟨phenyl with CF₃⟩ | red |

EXAMPLE 84

A laboratory kneader having a capacity of 250 parts by volume is charged with 25 parts of the pigment obtained in Example 30, 100 parts of finely ground sodium chloride and 30 parts of diacetone alcohol. The mixture is kneaded for 5 hours with cooling and then discharged into 4000 parts by volume of water. Sodium chloride and diacetone alcohol go into solution and the pigment precipitates. The suspension is filtered and the filter cake is washed thoroughly with water and dried in a vacuum drying cabinet at 80° C.

EXAMPLE 85

65 parts of stabilised polyvinyl chloride, 35 parts of dioctyl phthalate and 0.2 part of the pigment obtained in Example 84 are stirred together and then rolled for 7 minutes at 160° C. on a two-roll calender to produce an orange-red sheet of very good fastness to light and migration.

EXAMPLE 86

10 g of titanium dioxide and 2 g of the pigment obtained in Example 84 are ground for 48 hours in a ball mill with 88 g of a mixture of 26.4 g of coconut alkyd resin, 24 g of melamine/formaldehyde resin (50% solids content), 8.8 g of ethylene glycol monomethyl ether and 28.8 g of xylene. The resultant lacquer is sprayed onto an aluminium sheet, predried for 30 minutes at room temperature, and then stoved for 30 minutes at 120° C. A red finish of very good fastness to overspraying, light and atmospheric influences is obtained.

EXAMPLE 87

4 parts of the finely dispersed pigment of Example 84 are stirred into 20 parts of solvent of the following composition: 50 parts of Solvesso 150 (mixture of aromatic hydrocarbons), 15 parts of butylacetate, 5 parts of Exkin II (ketoxime-based levelling agent), 25 parts of methyl isobutyl ketone, 5 parts of silicone oil (1% in Solvesso 150). After complete dispersion has been attained (in about 15-60 minutes, depending on the type of stirrer), the binders are added, namely 48.3 parts of Baycryl L 530 (acrylic resin; 51% in xylene/butanol 3:1) and 23.7 parts of Maprenal TTX (melamine resin; 55% in butanol).

The batch is briefly homogenised and the resultant lacquer is then applied by conventional methods, such as spraying or dipping) or—particularly for the continuous coating of sheet metal—by the coilcoating method, and stoved (30 minutes at 130° C.). The red finishes obtained are distinguished by very good levelness, high gloss and excellent dispersion of the pigment, as well as by excellent fastness to atmospheric influences.

EXAMPLE 88

The procedure of Example 84 is repeated, except that 2.78 parts of Staybelite Resin (available from HERCULES) are added to the kneading stock. The resultant product is a pigment with a 10% resin content which can be more easily incorporated and having improved dispersibility.

What is claimed is:

1. A 1:1 metal complex of an azine of the formula

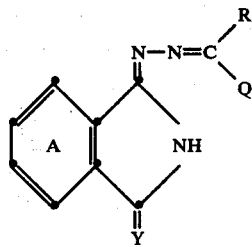

wherein
the ring A is unsubstituted or is substituted by two to four halogen atoms, by one or two alkyl of 1 to 4 carbon atoms, by one or two alkoxy of 1 to 4 carbon atoms, by phenyl, by phenoxy, by nitro, by benzoylamino, or by an alkanoylamino of 2 to 6 carbon atoms, Y is a radical of the formula

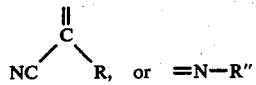

wherein R' is an alkoxycarbonyl, alkylcarbamoyl, carbamoyl, thiocarbamoyl or sulfamoyl group, a benzylcarbamoyl group, a phenylsulfamoyl or phenylsulfonyl group which is unsubstituted or substituted by halogen atoms or alkyl groups of 1 to 4 carbon atoms, a group of the formula

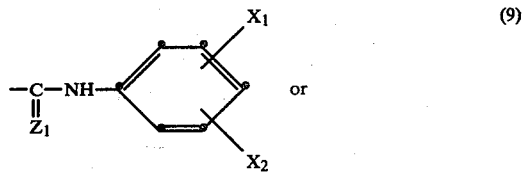

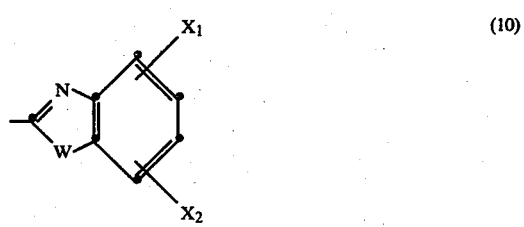

wherein $Z_1$ is an oxygen or a sulfur atom, $X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, benzoylamino, phenylcarbamoyl or phenylsulfamoyl or phenylazo group which is unsubstituted or substituted by chlorine or bromine atoms or methyl groups, and $X_2$ is a hydrogen, chlorine or bromine atom, an alkyl or alkoxy group of 1 to 4 carbon atoms, W is O, S, or NH, and R" is a radical of the formula (10), R is hydrogen, alkyl of 1 to 4 carbon atoms, phenyl or naphthyl, Q is the radical of a heteroaryl amine selected from the group consisting of 2-aminothiophene, 2-aminothiazole, 2-amino-5-nitrothiazole, 2-amino-5-methylsulfonylthiazole, 2-amino-5-cyanothiazole, 2-amino-4-methyl-5-nitrothiazole, 2-amino-4-methylthiazole, 2-amino-4-phenylthiazole, 2-amino-4-(4'-chloro)phenylthiazole, 2-amino-4-(4'-nitro)-phenylthiazole, 2-aminopyrazole, 3-amino-1-phenylpyrazole, 3-aminoindazole, 5-methylsulfonyl-2-aminothiazole, 5-benzoyl-2-aminothiazole, 4-aminoimidazole, 4,5-dicyano-2-aminoimidazole, 4,5-diphenyl-2-aminothiazole, 2-amino-3,4-thiadiazole, 2-amino-3,5-thiadiazole, 3-amino-1,2,4-triazole, 2-amino-3,4-oxadiazole, 3-aminopyridine, 2-aminopyridine-N-oxide, 2-amino-benzthiazole, 2-amino-6-chlorobenzthiazole, 2-amino-6-methylbenzthiazole, 2-amino-6-methoxybenzthiazole, 2-amino-6-chloro-4-nitrobenzthiazole, 2-amino-6-bromo-4-cyanobenzthiazole, 2-amino-6-cyano-4-methylbenzthiazole, 2-amino-6-methyl-4-nitrobenzthiazole, 2-amino-6-methoxy-4-nitro benzthiazole, 2-amino-6-butoxy-4-chlorobenzthiazole, 2-amino-4-chloro-5-methoxy-benzthiazole, 2-amino-4-bromo-6-methoxybenzthiazole, 2-amino-4,6-dichlorobenzthiazole, 2-amino-4,6-dibromobenzthiazole, 2-amino-4-methyl-6-(trifluoromethyl)-benzthiazole, 2-amino-4-methyl-6-propionyl-benzthiazole, 2-amino-4-chloro-6-methylsulfonyl-benzthiazole, 3-amino-benzisothiazole, 3-amino-5-chloro-benzisothiazole, 2-amino-3-cyanotetrahydrobenzthiaphene, 2-aminobenzimidazole, 2-amino-6-chlorobenzimidazole, 2-amino-6-bromo-benzimidazole, 2-amino-6-methyl-benzimidazole, 2-amino-6-methoxy-benzimidazole, 2-amino-6-ethoxy-benzimidazole, 2-amino-6-methylsulfonyl-benzimidazole, 2-amino-6-acetylaminobenzimidazole, 3-amino-isoindoleninone-1, 1,4-diaminophthalazine and 1-amino-4-chlorophthalazine, as well as their imine forms, or Q is a radical of the formula

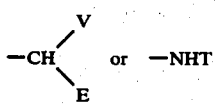

wherein E is an acyl group, an unsubstituted or a substituted carbamoyl or thiocarbamoyl group, V is an acyl, cyano or nitro group or an unsubstituted or substituted carbamoyl or thiocarbamoyl group, T is a radical of the formula

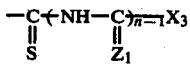

wherein $Z_1$ is an oxygen or a sulfur atom, n is 1 or 2, $X_3$ is an alkyl, cycloalkyl, aralkyl or aryl radical, or an amino group which is unsubstituted or substituted by an alkyl, cycloalkyl, aralkyl or aryl radical, and the metal is selected from the group consisting of zinc, cadmium, manganese, cobalt, iron, copper and nickel.

2. A 1:1 metal complex of an azine according to claim 1 wherein ring A is unsubstituted and Q is the radical of the formula

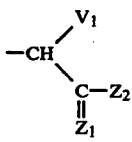

wherein $V_1$ is an acetyl cyano, benzoyl or carbamoyl group, an alkylcarbamoyl group containing 2 to 6 carbon atoms, a benzylcarbamoyl group or a group of the formula

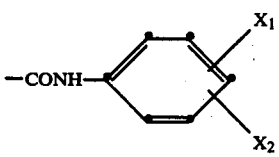

$X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, benzoylamino, phenylcarbamoyl or phenylsulfamoyl or phenylazo group which is unsubstituted or substituted by chlorine or bromine atoms or methyl groups, and $X_2$ is a hydrogen, chlorine or bromine atom, an alkyl or alkoxy group of 1 to 4 carbon atoms, $Z_1$ is an oxygen or a sulfur atom, $Z_2$ is a phenyl radical or the group

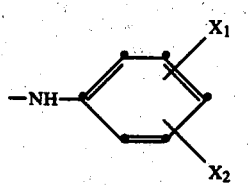

where $X_1$ and $X_2$ are defined above.

3. A 1:1 metal complex of an azine according to claim 1 wherein ring A is unsubstituted and Q is a radical of the formula

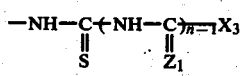

wherein n is 1 or 2, $Z_1$ is an oxygen or a sulfur atom and $X_3$ is an amino group which is unsubstituted or substituted by a group of the formula

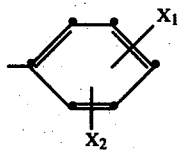

$X_1$ is a hydrogen, chlorine or bromine atom, a nitro, trifluoromethyl, carbamoyl or sulfamoyl group, an alkyl, alkoxy or alkylsulfamoyl group of 1 to 4 carbon atoms, an alkanoylamino, alkylcarbamoyl or alkoxycarbonyl group of 2 to 6 carbon atoms, a phenoxy, benzoylamino, phenylcarbamoyl or phenylsulfamoyl or phenylazo group which is unsubstituted or substituted by chlorine or bromine atoms or methyl groups, and $X_2$ is a hydrogen, chlorine or bromine atom, an alkyl or alkoxy group of 1 to 4 carbon atoms.

4. The compound according to claim 1 of the formula

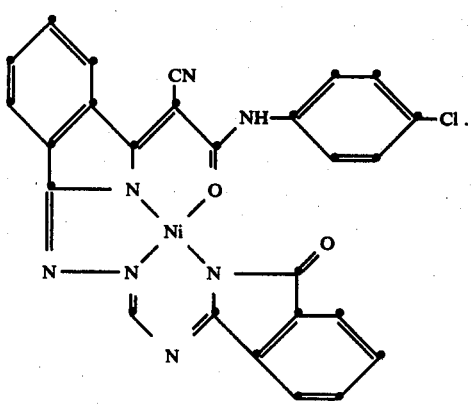

5. The compound according to claim 1 of the formula

7. The compound according to claim 1 of the formula
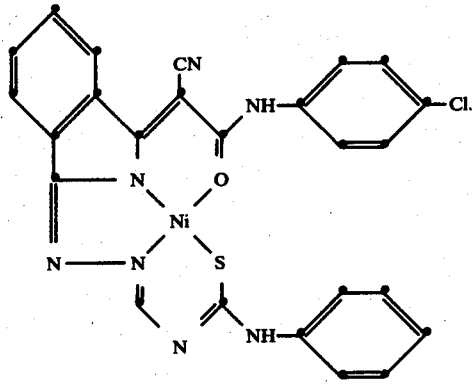
6. The compound according to claim 1 of the formula
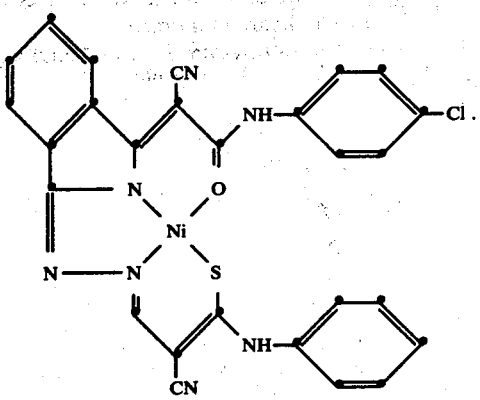
8. The compound according to claim 1 of the formula
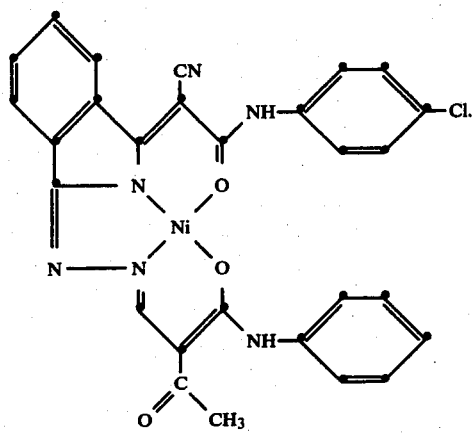
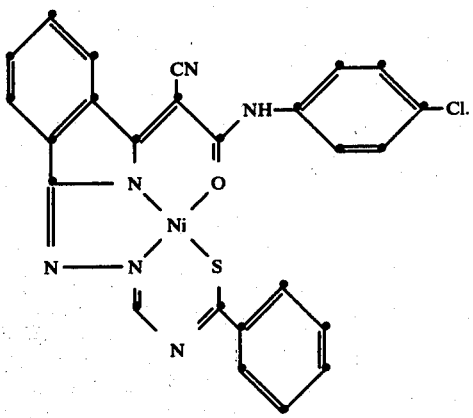
* * * * *